United States Patent [19]

Morgan, Jr. et al.

[11] Patent Number: 5,084,396

[45] Date of Patent: * Jan. 28, 1992

[54] ENHANCED PRODUCTION OF ANTIBODIES UTILIZING INSOLUBILIZED IMMUNE COMPLEXES

[75] Inventors: A. Charles Morgan, Jr., Edmonds; Clive S. Woodhouse; Robert F. McIntyre, both of Seattle, all of Wash.

[73] Assignee: Neorx Corporation, Seattle, Wash.

[*] Notice: The portion of the term of this patent subsequent to Nov. 7, 2006 has been disclaimed.

[21] Appl. No.: 579,627

[22] Filed: Sep. 7, 1990

Related U.S. Application Data

[63] Continuation of Ser. No. 391,286, Aug. 8, 1989, abandoned, which is a continuation-in-part of Ser. No. 24,632, Mar. 11, 1987, Pat. No. 4,879,225, which is a continuation-in-part of Ser. No. 876,828, Jun. 20, 1986, abandoned.

[51] Int. Cl.$^5$ .................... G01N 33/563; A61K 39/00
[52] U.S. Cl. ........................................ 436/513; 424/88
[58] Field of Search ............................ 436/513; 424/88

[56] References Cited

U.S. PATENT DOCUMENTS 4,829,225 11/1989 Morgan, Jr. et al. ................. 424/88

Primary Examiner—Robert A. Wax
Assistant Examiner—Bradley L. Sisson
Attorney, Agent, or Firm—Debra K. Leith

[57] ABSTRACT

A method for enhancing production of antibodies through immunization with insolubilized immune complexes is disclosed. Purified antigen or heterogeneous antigen mixtures may be combined with polyclonal or monoclonal antibody and the resultant complex bound to an insolubilized matrix to form insolubilized immune complexes. Methods for improving the immunogenicity of a soluble antigen and for producing monoclonal anti-idiotypic antibodies are also disclosed. Monoclonal antibodies that are specific for a distinct, as yet unrecognized epitope may be produced by another disclosed method. Insolubilized immune complexes, comprising antigen and antibody that is ether directly linked to Sepharose ® or absorbed onto insolubilized protein A, and immunosorbents, comprising antibody absorbed onto insolubilized protein A, are also disclosed.

16 Claims, 5 Drawing Sheets

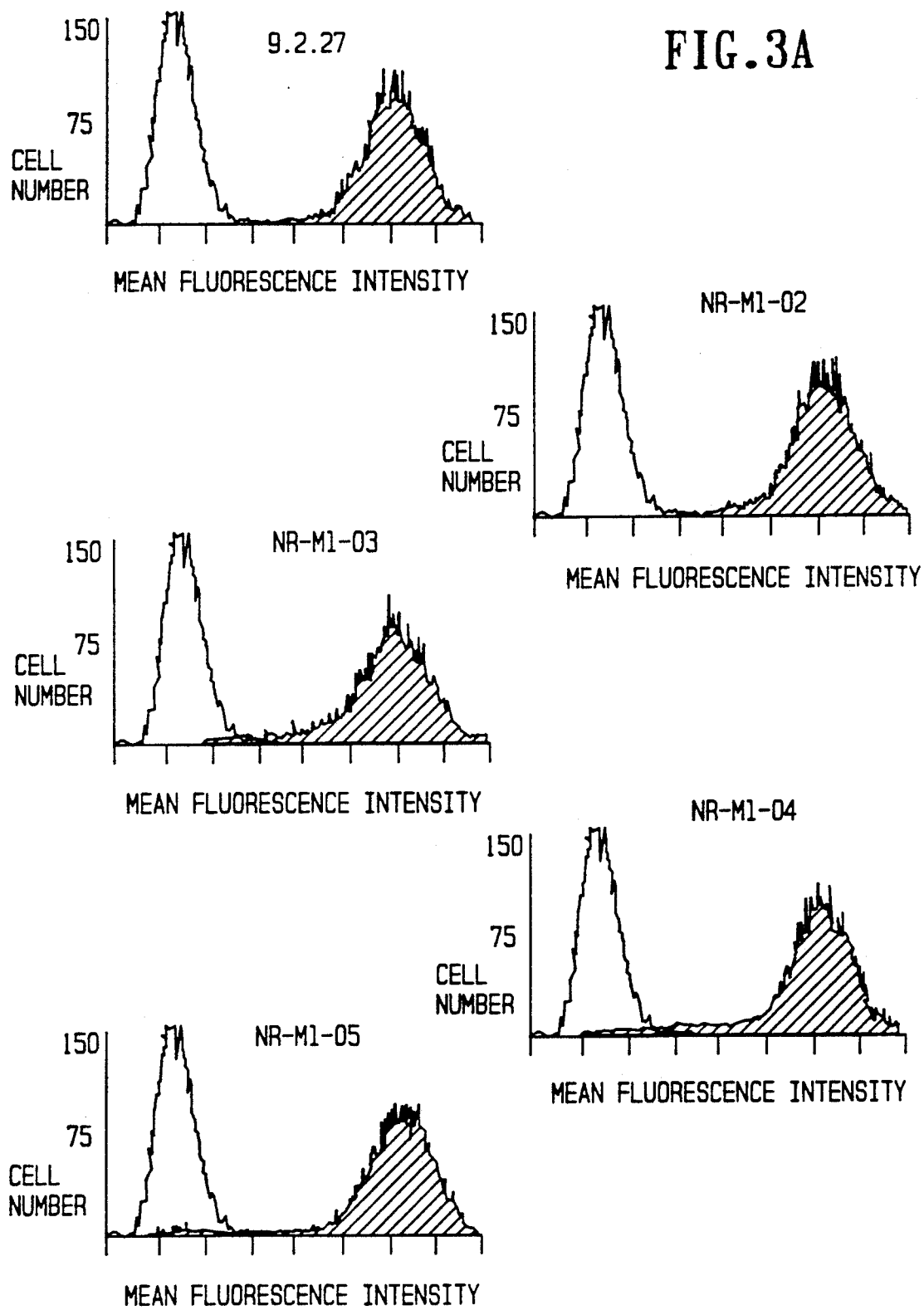

ENHANCED PRODUCTION OF ANTIBODIES UTILIZING INSOLUBILIZED IMMUNE COMPLEXES

CROSS-REFERENCE TO RELATED APPLICATIONS

This application is a continuation application of U.S. patent application Ser. No. 07/391,286, filed Aug. 8, 1989, now abandoned, which is a continuation-in-part application of allowed U.S. patent application Ser. No. 024,632, filed Mar. 11, 1987, which issued as U.S. Pat. No. 4,879,225, which is a continuation-in-part application of U.S. patent application Ser. No. 876,828, filed on June 20, 1986, now abandoned.

TECHNICAL FIELD

The present invention is for a method of enhanced production of antibodies to a variety of antigens utilizing insoluble immune complexes. Purified antigen, enriched antigen present with other contaminating antigens, and heterogeneous mixtures are employed as sources of antigen. Polyclonal monospecific, polyclonal polyspecific, or monoclonal antibodies are combined with antigen and a particulate, insoluble carrier, such as protein A-Sepharose ® or methacrylate beads, to form insolubilized immune complexes. Antibodies to the antigen component of such complexes are produced with high efficiency, and in some cases, with improved specificity over original antisera or monoclonal antibodies.

BACKGROUND ART

A variety of protocols in the prior art have been employed for production of monoclonal and polyclonal antibodies to glycoproteins, to glycolipids and to tumor-associated antigens. For example, production of monoclonal antibodies can utilize whole cells, which are a highly immunogenic vehicle. This method, however, is fraught with the problem of a low efficiency in producing antibodies of interest. In addition, purified, soluble antigens are poorly immunogenic in mice, in contrast to the same immunogens in other species such as rabbits and sheep.

Presentation of an antigen in an insoluble form may improve immunogenicity of soluble antigen preparations in mice. For example, alum precipitation of carcinoembryonic antigen in some cases enhances immunogenicity. However, adjuvants are often required to achieve desired levels of antibody production. Traditionally, adjuvants, such as Freund's, have been admixed with soluble antigen preparations for immunizing rabbits or goats. However, adjuvant is oftentimes ineffective in mice; even though it may produce detectable titers of antibody, the yield of antigen-specific hybridomas is low. The present invention discloses an insolubilized immunogen that is effective in producing antigen-specific hybridomas.

Soluble immunogen preparations described in the prior art also usually require a great deal of effort for isolation of sufficient quantities of purified antigen. Most protocols for immunizing with soluble antigens utilize 50-100 μg of purified antigen. Preparing this dosage of antigen involves considerable effort in biochemical purification, because most cell surface or cytoplasmic antigens are produced only in small amounts by cells. An advantage of the present invention is that it provides a process for enrichment of a given antigen from a heterogeneous mixture, thus reducing the need for purification. The term "enrichment," as used herein, means an increased concentration of the antibody or antigen of interest.

Another advantage provided by this invention is the production of monoclonal antibodies to epitopes on the same antigen that ar distinct from the epitope identified by the antibody used in preparation of the immunogen. The need for antibodies to multiple epitopes of an antigen has been previously demonstrated. For example, it has been shown that more than one epitope can exist within a glycoprotein species, and that different combinations of epitopes can be found on different subpopulations of glycoprotein molecules. Thus, not all epitopes have to be on all the glycoprotein molecules and/or have the same distribution within a given tissue. More specifically, the inventors have found that the degree of antigenic heterogeneity in a human melanoma-associated antigen system is dependent upon the epitope recognized by the monoclonal antibody (Morgan et al., *Mol. Immunol.* 23:193-200, 1986). One monoclonal antibody (MAb), that recognized an epitope displayed on most of the melanoma glycoprotein molecules, had less antigenic heterogeneity than a MAb that recognized an epitope present only on a subpopulation of glycoprotein molecules. Utilizing monoclonal antibodies to carcinoembryonic antigen (CEA), the CEA preparation can be subdivided into populations of molecules bearing unique epitopes. This also has been demonstrated with monoclonal antibodies to Class II histocompatibility antigens (HLA-DR antigens). Thus, the generation of unique antibodies to specific epitopes on a given antigen is useful for the optimization of therapeutic applications of monoclonal antibodies involving delivery of radioisotopes, drugs, or toxins to a target tumor.

As with antigen purification, the prior art method of producing monoclonal antibodies to specific epitopes of a given antigen is laborious. The prior art methodology involves immunization with soluble purified antigen isolated by a series of steps: production of large quantities of a given monoclonal antibody, purification of that antibody, insolubilization of that antibody on an insoluble matrix (e.g., Sepharose ®, an agarose gel, optionally cross-linked, in bead-form), and typically utilization of at least one other chromatography procedure (e.g., lectin affinity chromatography, ion exchange chromatography, gel filtration or hydrophobic chromatography) in combination with monoclonal antibody affinity chromatography to purify the antigen from a heterogeneous antigen mixture. This method is expensive and time-consuming, and requires large numbers of cells as the source of the impure antigen. In addition, once isolated, the soluble antigen preparation is poorly immunogenic in mice. Thus, there is a need in the art for more efficient and less time-consuming methods of generating monoclonal antibodies to epitopes of antigens distinct from those recognized by existing monoclonal antibodies. Within the present invention, the source of antigen need not be purified, and yet immunogenicity is enhanced.

There is also a need in the art for a method of producing monoclonal antibodies to antigens for which polyclonal antisera exist. If these polyclonal antisera do exist, although in small amounts, in low titers, or in polyspecific form (containing many antibodies of different specificities), they may be used in the present invention for production of monoclonal antibodies. In many cases, the amounts of these antisera are limited, are insufficient for antibody affinity chromatography, and are thus useless for immunization procedures involving soluble purified antigen. An additional benefit of the immunization process of the present invention is the ability to generate monoclonal antibodies of different specificity compared to the polyclonal antiserum used in the immunization.

There is also a need in the art for a method for efficiently producing monoclonal anti-idiotypic antibodies, which recognize the antigen-combining site of a monoclonal antibody (MAb) of murine origin. It has been postulated and subsequently verified in certain animal models that anti-idiotypic antibodies can act to regulate the immune response in both a positive and a negative manner. In certain instances, anti-idiotypic antibodies can substitute for purified antigen in the production of vaccines, thus eliminating the need for biochemical purification of a given antigen.

As shown in certain animal models, anti-idiotypic antibodies utilized as vaccines may prove useful in adjuvant therapy of cancer. The field is handicapped by difficulties in producing monoclonal antibodies of murine origin to other murine monoclonal antibodies. Murine MAbs to human and rabbit antibodies have been successfully produced. However, most MAbs to tumor-associated antigens are of mouse origin. The combining site of these tumorspecific murine MAbs may be poorly immunogenic, presumably due to self-tolerance induced by common sequences within the Fc region. It appears that species distinction within the Fc region may result in enhanced immunogenicity of the antigen combining site (idiotope). In the present invention, the use of an immunosorbent enhances the generation of antibodies to the idiotope of a monoclonal antibody.

Another advantage of the present invention is that it provides an efficient technique for generating a battery of monoclonal antibodies that are directed against multiple epitopes of a given antigen. This methodology facilitates the production of monoclonal antibodies that recognize immunorecessive epitopes of an antigen. As a result, a variety of monoclonal antibodies may be bound to one target cell or antigen, thereby enhancing the delivery of a higher dose of conjugated toxin or radioisotope to a target site. Delivery of an increased concentration of immunoconjugates improves cytotoxicity or imaging properties, because multiple distinct epitopes of a target cell can be bound. In addition, the availability of a multiplicity of monoclonal antibodies will permit targeting of a variety of epitopes, some of which may be unique to a particular target cell. This unique binding capability may allow selection of monoclonal antibodies that exhibit little or no cross-reactivity with epitopes of normal cells, which in turn might permit administration of higher doses of immunoconjugates.

DISCLOSURE OF THE INVENTION

The present invention discloses a method for enhancing production of antibodies, comprising the steps of absorbing antibody onto insolubilized protein A, thereby forming an immunosorbent; combining an antigen with the immunosorbent, forming an insolubulized immune complex; immunizing an animal with the insolubilized immune complex; and collecting antiserum from the immunized animal.

A related aspect of the present invention discloses a method for improving the immunogenicity of a soluble antigen, thereby enhancing production of specific monoclonal antibodies, comprising the steps of absorbing antibody onto insolubilized protein A, thereby forming an immunosorbent; combining the soluble antigen with the immunosorbent, forming an insolubilized immune complex; immunizing an animal with the insolubilized immune complex; fusing spleen cells from the immunized animal to myeloma cells to form hybridomas capable of producing monoclonal antibodies to the soluble antigen; culturing the hybridomas to produce the monoclonal antibodies: and collecting the monoclonal antibodies as a product of the hybridomas.

A further aspect of the present invention discloses a method for producing monoclonal antibodies specific for an epitope distinct from that recognized by an existing monoclonal antibody, comprising the steps of absorbing an existing monoclonal antibody directed against a first epitope of a polyvalent antigen onto insolubilized protein A, thereby forming an immunosorbent; combining the immunosorbent with the antigen, forming an insolubilized immune complex wherein the first epitope is masked by the existing monoclonal antibody; immunizing an animal with the insolubilized immune complex; fusing spleen cells from the immunized animal to myeloma cells to form hybridomas capable of producing second monoclonal antibodies to the particular epitope; culturing the hybridomas to produce the second monoclonal antibodies specific for the particular epitope; and collecting the second monoclonal antibodies as a product of the hybridomas.

Another aspect of the present invention discloses a method for producing monoclonal anti-idiotypic antibodies, comprising the steps of absorbing a first antibody onto insolubilized protein A, thereby forming an immunosorbent; immunizing an animal with the immunosorbent; fusing spleen cells from the immunized animal to myeloma cells to form hybridomas capable of producing monoclonal antibodies to an idiotope of the first antibody; culturing the hybridomas to produce the monoclonal antibodies; and collecting the monoclonal antibodies as a product of the hybridomas.

Insolubilized immune complexes for use as immunogens and immunosorbents for use in producing monoclonal anti-idiotypic antibodies are also disclosed. In addition, a variety of monoclonal antibodies that bind to multiple epitopes of a tumor-associated antigen are disclosed.

A further aspect of the present invention is monoclonal antibody capable of binding to an epitope of human melanoma-associated proteoglycan that is not recognized by antibody 9.2.27. Also included are continuous hybrid cell lines capable of producing such antibodies.

These and other aspects of the invention will become apparent upon reference to the following description and attached drawings.

BRIEF DESCRIPTION OF THE DRAWINGS

FIG. 1A depicts reactivity with alpha-2 macroglobulin from melanoma spent culture medium; FIG. 1B depicts reactivity with purified alpha-2 macroglobulin from normal human serum; and FIG. 1C depicts reactivity with bovine alpha-2 macroglobulin. One group (Group I) of monoclonal antibodies generated using melanoma alpha-2 macroglobulin reacted with alpha-2 macroglobulin obtained from all three sources. Another group (Group II) reacted only with the melanoma and normal human serum forms of alpha-2 macroglobulin. A third group (Group III) reacted only with the melanoma form of alpha-2 macroglobulin.

FIG. 3 shows flow cytometry of melanoma-reactive monoclonal antibodies tested against (A) proteoglycan—positive and (B) proteoglycan-negative A375 melanoma cells.

FIG. 3A illustrates binding of five anti-melanoma antibodies (9.2.27, NR-ML-02, NR-ML-03, NR-ML-04 and MR-ML-05) to A375 M/M proteoglycan-positive cells.

BEST MODE FOR CARRYING OUT THE INVENTION

Figure 1:
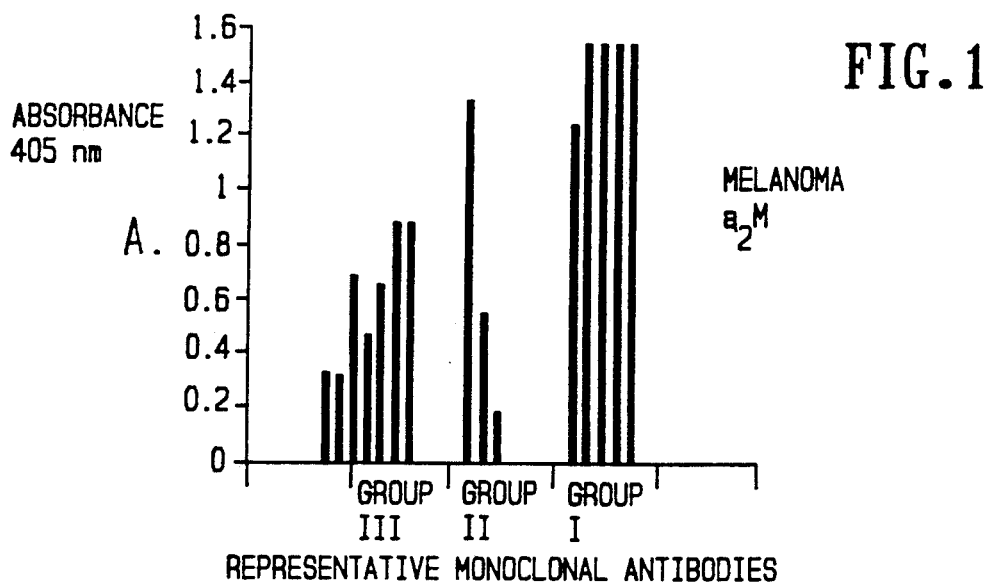
FIG. 1 depicts the specificity of monoclonal antibodies generated to melanoma alpha-2 macroglobulin when tested against three different sources of alpha-2 macroglobulin in an ELISA.
Figure 1:
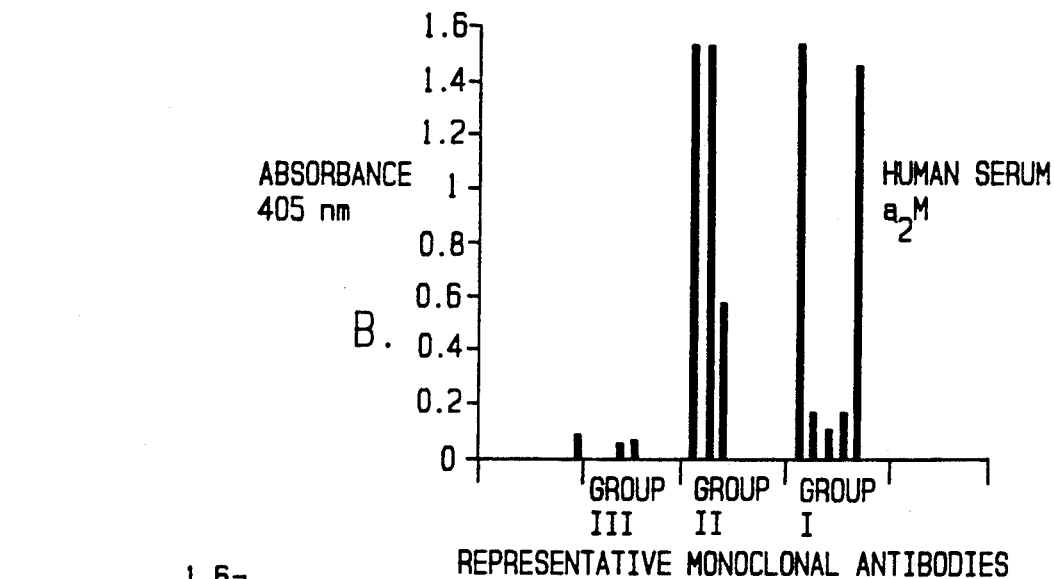
Figure 1:
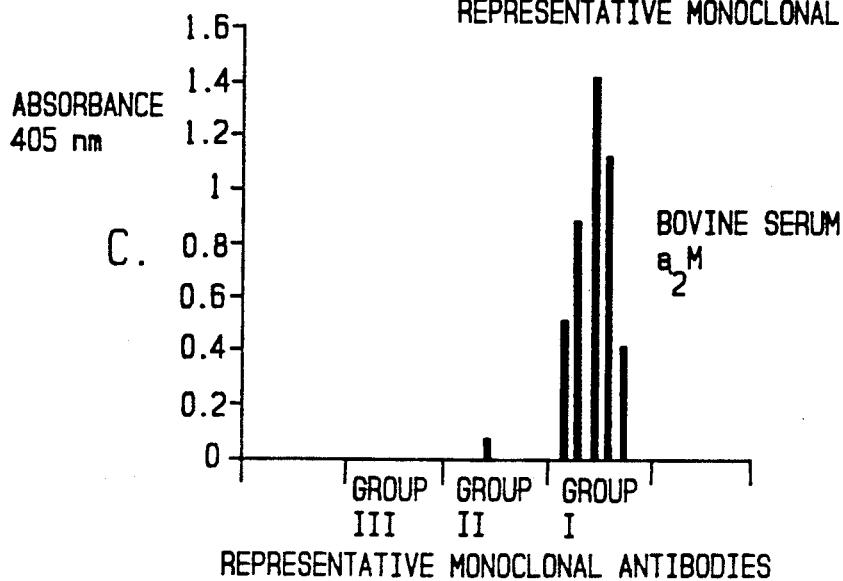

The method of the present invention for enhanced production of antibodies circumvents prior art antigen purification steps, and also increases the number of antigen-reactive hybridomas over that obtained by prior art methodology, thus increasing the overall efficiency of generating monoclonal and polyclonal antibodies to a desired antigen.

In order to carry out this invention, a relative amount of the desired antigen within the antigen mixture needs to be determined. Thus, cell surface extraction is carried out with agents such as lithium diiodosalicylate, butanol, isotonic urea, non-ionic detergents, or ionic detergents to create a soluble extract. For example, non-detergent extractions are often used for preparation of peripheral membrane proteins. The soluble extract is an enriched source of antigen, when the target antigen represents 1% (w/w) or more of the extract preparation. However, less enriched extract preparations can also be utilized.

The extract preparation is then assayed for protein content. 100 ng to 10 µg of protein in phosphate-buffered saline is added to polyvinyl microtiter plates in 100 µl volumes. Following drying overnight, the presence of the desired antigen is then detected by binding of polyclonal antisera or monoclonal antibody to the solid-phase target antigen by ELISA techniques. For comparison, similar extracts from non-antigen-bearing cells can be utilized. The amount of antigen can be expressed in titers by dilution of the target protein in wells. Having established the presence of the desired antigen in the extract preparation, one would titer the antibody or antibody sources versus the solid-phase antigen. An antiserum or monoclonal antibody for preparation of the immunogen would be selected on the basis of highest titer, production in an appropriate species of animal, and/or subclass of murine immunoglobulin capable of binding to protein A-Sepharose ®.

Typical protein concentrations used for forming insolubilized immune complexes are: 20 µg of polyclonal antibody per 20 µl of protein A-Sepharose ® (packed volume). Alternatively, 5-50 µg of MAb immunoglobulin can be insolubilized on the same volume of protein A-Sepharose ®. An immunosorbent is formed by absorption, which is carried out at room temperature for 2 hours, with end-over-end rotation, followed by washing in phosphate-buffered saline (PBS).

In an alternative embodiment, the immunosorbent is made by linking the desired antibody directly to CNBr-Sepharose ®. In yet another embodiment, the desired antibody is immobilized using anti-immunoglobulin-coated methacrylate beads or protein A-methacrylate beads.

Certain characteristics of the inert, immobilizing matrix may influence the selection of a particular matrix for a particular purpose. For instance, while protein A-Sepharose ®-bound immune complexes may be suitable for intraspenic or intraperitoneal injection, the size of the protein A-Sepharose ® bead renders such complexes impractical for intravenous administration in mice. Immune complexes insolubilized with anti-immunoglobulin-coated methacrylate beads or protein A-methacrylate beads are better suited to murine intravenous administration, because the methacrylate beads are smaller in size than Sepharose ®. It would be evident to one skilled in the art of immunology that a variety of inert, insoluble matrices having antibody-binding capabilities would be suitable for use within the present invention.

The immunosorbent is then utilized to absorb the antigen extract. In order to minimize the nonspecific adherence of extract proteins to the immunosorbent, the extract is preabsorbed with normal immunoglobulin-protein A-Sepharose ®. Normal immunoglobulin can be obtained from rabbit or goat serum, or from a nonspecific mouse monoclonal antibody of the same subclass as the one used for absorption of the specific antigen. Preabsorptions are carried out in three steps: (1) incubation of the nonspecific immunosorbent and extract preparation at room temperature for 2 hours; (2) transfer of the extract preparation to an aliquot of fresh nonspecific immunosorbent for an additional 2 hours; and (3) transfer of the supernatant to a third aliquot of nonspecific immunosorbent, with incubation overnight at 4° C. Following this depletion of nonspecific binding components, the antigen preparation is retitered with antiserum or MAb to the specific antigen, and can be frozen in aliquots for subsequent preparation of the insolubilized immune complex.

In vivo stability of the insolubilized immune complex is enhanced where the antibody and protein A are cross-linked by treatment with the N-succinimidyl ester of 4-azidosalicylic acid (NHS-ASA) (Tae et al., Anal. Biochem. 121: 286, 1982). Alternatively, the antibody and antigen can be cross-linked by treatment with NHSASA. Cross-linking will prevent dissociation in sera, thus increasing the in vivo retention of the immune complex.

The amount of total protein added to the insolubilized antibody is approximated on the basis of relative enrichment of the given antigen as assessed by ELISA. Thus, if the antigen preparation is a purified antigen, then 250 ng or less of pure antigen is utilized with each immunosorbent and each immunization. If the appropriate antigen constitutes only 1% of the preparation, then typically 5-10 μg of the antigen preparation is utilized. If the soluble extract employed as the source of antigen is a heterogeneous antigen mixture containing a concentration of the given antigen which is less than 1%, then 10 μg or more of the extract is utilized for absorption to the insolubilized antibody. Following incubation at 4° C. for 2-14 hours, the insolubilized immune complex is then washed with PBS and injected into the peritonea of BALB/c mice.

If intrasplenic immunization is desired, the immunosorbent is homogenized in a Dounce apparatus to produce smaller Sepharose ® particles before intrasplenic injection with a 27-gauge needle. While intraperitoneal immunizations are scheduled weekly for 3-6 weeks, typically only one intrasplenic injection of 5-10 μg of the antigen preparation is required. For both intraperitoneal and intrasplenic immunizations, spleen cells are harvested 3-7 days after the final immunization, and hybridomas are produced by standard techniques. Hybridoma screenings are done by ELISA against the original antigen target mixture used for immunization, as well as against target antigen mixtures known to not contain the antigen of interest.

Insolubilized immune complexes may also improve the immunogenicity of poorly immunogenic soluble antigens, thus allowing production of high-titer antiserum or specific monoclonal antibodies which were previously unattainable. For instance, trichothecenes represent a species of mycotoxins produced by soil fungi of the class *Fungi imperfecti* or isolated from *Baccharus megapotamica*. Trichothecenes are extremely potent cytotoxins that act at the ribosomal level to inhibit either initiation, elongation or termination of protein synthesis. In some respects, trichothecenes resemble microbial or plant toxins, but in contrast to other "natural toxins", trichothecenes are very small molecules (i.e., 400-600 daltons). While the small size of trichothecenes offers certain advantages for therapeutic applications, that same size combined with potent cytotoxic properties renders generation of anti-trichothecene antibodies difficult, if not impossible.

Within the present invention, anti-trichothecene antibodies are generated by immunizing experimental animals with insolubilized trichothecene-targeting protein conjugates. The targeting protein displays minimal or no reactivity with normal tissues. A preferred targeting protein is a monoclonal antibody that is characterized as relatively anti-tumor specific.

To further illustrate this embodiment of the invention, a targeting protein is covalently linked to one or more trichothecene molecules. In order to further enhance immunogenicity, the conjugate is presented in insolubilized form (i.e., on protein A-Sepharose ® or anti-immunoglobulin-coated beads). When injected into a recipient, even if some dissociation of insolubilized conjugate or insolubilized immune complex occurs in vivo, the released targeting protein-trichothecene conjugate would not bind to normal cells. Instead, any released targeting protein-trichothecene conjugate would be cleared by the recipient's foreign protein clearance mechanisms (assuming the targeting protein is "foreign" to the recipient). Thus, by immunologically presenting a trichothecene in insolubilized conjugate or insolubilized immune complex form, the toxicity of the trichothecene component can be greatly reduced or eliminated. In addition, the targeting protein component of the conjugate may function as a carrier for the "hapten-like" small trichothecene (<600 daltons), increasing trichothecene immunogenicity.

When antigen is incorporated into an insolubilized immune complex through binding of antigen to a known monoclonal antibody, the epitope recognized by the monoclonal antibody is presumably effectively masked. Immunization with antigen in insolubilized immune complexes with a masked epitope permits more efficient production of second generation monoclonal antibodies, which are directed against non-masked epitopes of the antigen. This technique is useful for generating monoclonal antibodies directed against tumor-associated epitopes of non-tumor- associated antigens. Monoclonal antibodies which recognize different epitopes of a given antigen might also be useful in differentiating oncogene and proto-oncogene products.

For production of monoclonal anti-idiotypic antibodies, a human or mouse monoclonal antibody is absorbed to protein A-Sepharose ®. The resultant immunosorbent is washed free of unbound antibody and is then used to immunize rodents. The hybridomas produced by fusion of immunized spleen cells and myeloma cells are screened by one of two methods. If rats are immunized with an insolubilized murine antibody on protein A-Sepharose ®, then hybridoma screening is done by an indirect ELISA using anti-rat peroxidase-conjugated reagents. If mice are immunized, then hybridoma screening is done by inhibition of binding of enzyme-labeled specific antibody (idiotype) to target cells (antigen) by putative anti-idiotypic antibodies.

The success of insolubilized immune complex immunogens could be due to a number of factors. The first is the relative enrichment of a given antigen by absorption to specific antibody. However, this does not suggest a rationale for the success of experiments utilizing polyclonal antisera as a source of immobilizing antibody. With polyclonal antisera, one would not expect this method to yield a great enrichment of a given antigen. A second factor in this success could be the adjuvanicity of insolubilized protein A, which may play a role in enhancing B-cell differentiation and proliferation. Soluble protein A is a well-known mitogen and differentiation agent for mouse B-cells. Protein A could act as a secondary proliferation signal and cause clonal expansion of B-cells presensitized to the target antigen. A third factor in the success of these immunogens might be that immune complexes may be a natural mode of regulation of immune responses. Many studies have indicated that antigen-antibody complexes traffic to follicular areas of lymph nodes and are bound preferentially to Fc receptors. Concentration and subsequent presentation by macrophages can lead to sensitization of B lymphoid cells, and thus to an enhancement of immune responsiveness. It would be expected that in vivo, insolubilized immune complexes are gradually released due to competition for protein A binding with the host's immunoglobulin.

EXAMPLE 1

Generation of monoclonal antibodies utilizing monospecific polyclonal antiserum

Alpha-2 macroglobulin ($\alpha_2$m) has been shown to be synthesized by human melanoma cells and secreted into spent culture medium (Morgan, JNCI 72:7, 1984). The identification of this molecule was performed using monospecific polyclonal antisera raised to the normal serum form of $\alpha_2$m. The melanoma cell form of $\alpha_2$m was shown to be of approximately the same molecular weight, and to have the same subunit composition as, serum $\alpha_2$m. Monoclonal antibodies were then generated to the melanoma cell form of alpha-2 macroglobulin utilizing an insoluble complex of the polyclonal antisera to serum $\alpha_2$m and spent culture medium containing the melanoma form of $\alpha_2$m. The specificity of these anti-$\alpha_2$m MAbs is shown in FIG. 1. Data from three groups of antibodies are shown. The first group reacted with alpha-2 macroglobulin from normal serum, melanoma spent medium, and bovine serum. The second group of MAb recognized only the human forms of alpha-2 macroglobulin in melanoma spent medium and in normal serum. The third group of antibodies reacted only with the melanoma cell form of $\alpha_2$m, and did not recognize either the normal human or bovine serum forms. These results demonstrate that monoclonal antibody production can be enhanced by utilizing monospecific polyclonal immune complexes, and that the monoclonal antibodies generated can be selective for a tumor cell form of an antigen rather than for its normal serum counterpart, even though the tumor cell form is molecularly very similar to the normal serum antigen.

Figure 2:
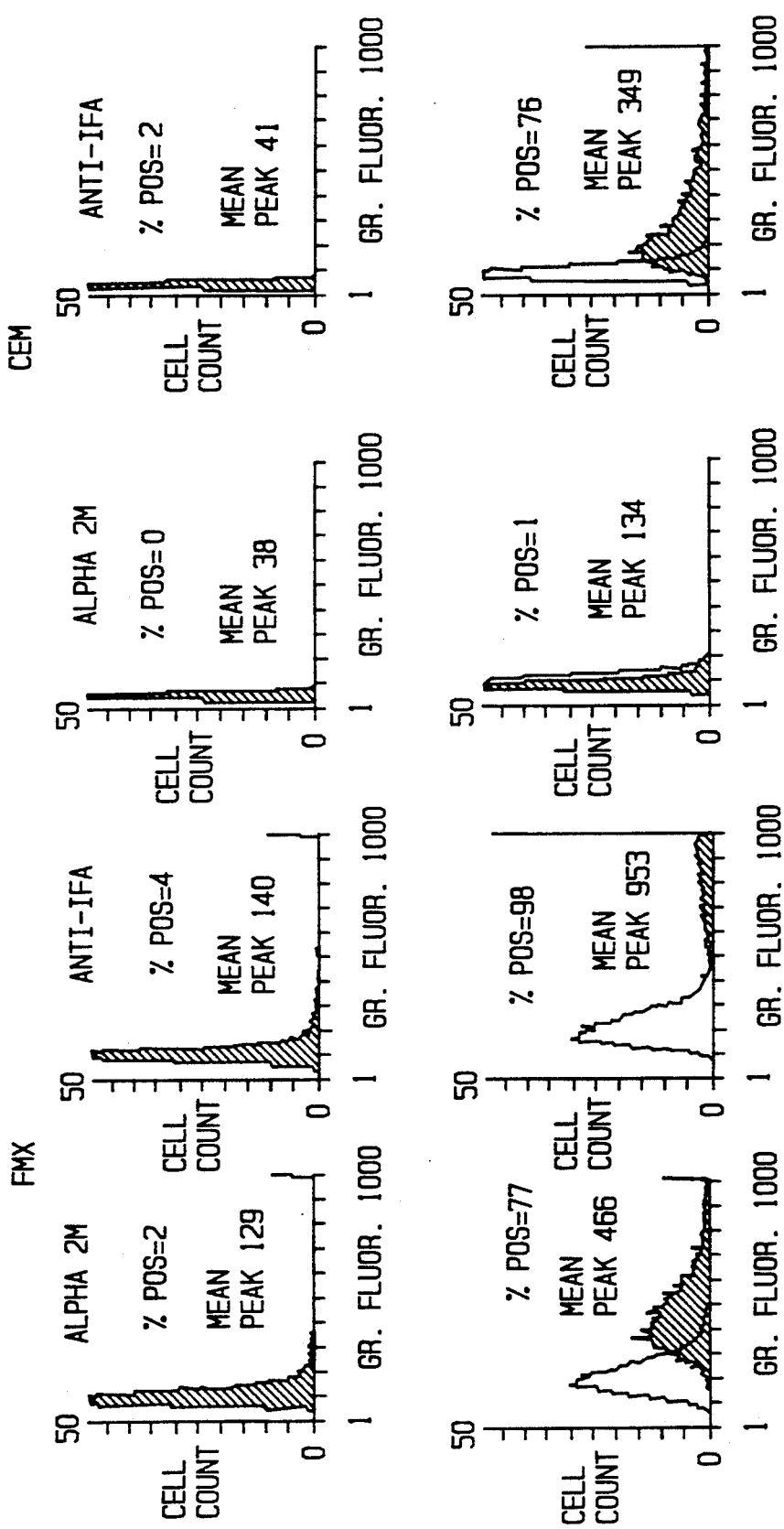
FIG. 2 depicts flow cytometry of monoclonal antibody to alpha-2-macroglobulin. Top panels indicate CEM (human T cell) or FMX (human melanoma) cells incubated with monoclonal antibodies reactive with alpha-2-macroglobulin (alpha 2M) or intermediate filament antigens (anti-IFA), and stained with FITC-goat anti-mouse immunoglobulin. Bottom panels indicate FMX and CEM cells permeabilized with lysolecithin prior to incubation with alpha 2M or Anti-IFA. Anti-IFA is a positive control for intracellular, non-cell surface antigens.

The specificity of anti-$\alpha_2$m monoclonal antibodies was further characterized by flow cytometry. A human melanoma cell line that synthesizes $\alpha_2$m (FMX) was incubated with anti-$\alpha_2$m MAb. In order to detect $\alpha_2$m that is synthesized, but not expressed on the cell surface, FMX cells were also permeabilized with lysolecithin prior to incubation with MAb. Intact and permeabilized human T cells (CEM) that lack $\alpha_2$m served as a negative control. Anti-intermediate filament MAb acted as a positive control for access to intracellular antigens after permeabilization. FIG. 2 demonstrates binding of anti-$\alpha_2$m MAb to intra-cellular $\alpha_2$m only, indicating that $\alpha_2$m is not expressed on the surface of FMX cells. CEM cells were consistently nonreactive, demonstrating that endocytosis of bovine $\alpha_2$m from the culture medium did not interfere with the assay.

EXAMPLE 2

Generation of monoclonal antibodies to transforming growth factor using polyspecific polyclonal antibody and a heterogeneous antigen preparation Alpha transforming growth factor ($\alpha$TGF) may be important in the control of tumor growth, and in particular, in endocrine growth regulation. Monoclonal antibodies against $\alpha$TGF have been difficult to generate, even though synthetic peptides are available which represent all or part of this peptide growth factor's amino acid sequence. Polyspecific rabbit antiserum raised against whole melanoma cells was titrated against a preparation TGF isolated by reverse-phase HPLC from melanoma urine. The antiserum displayed a low titer (1:4) versus the $\alpha$ TGF preparation, which was approximately 20% $\alpha$TGF and 80% other contaminating urinary proteins by SDS-polyacrylamide gel electrophoresis. This antiserumantigen preparation was bound to protein A-Sepharose ®, and monoclonal antibodies were generated utilizing six weekly immunizations. Examples of hybridoma clones derived from these fusions are shown in Table 1.

TABLE 1

| MONOCLONAL ANTIBODIES REACTIVE WITH ALPHA TRANSFORMING GROWTH FACTOR | |
|---|---|
| Reactivity Pattern* | Percent of Clones |
| TGF+, EGF+ | 23 |
| TGF−, EGF+ | 69 |
| TGF+, EGF− | 8 |

*Monoclonal antibodies were assayed by solid-phase ELISA for binding to urinary $\alpha$TGF from melanoma patients and to purified human EFG.

Most of the monoclonal antibodies generated in response to the urinary $\alpha$TGF preparation reacted with human epidermal growth factor (EGF) as well as with $\alpha$TGF. Some monoclonal antibodies raised to urinary $\alpha$TGF reacted preferentially with EGF, but not with a 17-amino acid peptide derived from the C-terminus of $\alpha$TGF. One monoclonal antibody displayed specificity for $\alpha$TGF and was nonreactive with human EGF. These results demonstrate that a non-immunogenic peptide growth factor such as $\alpha$TGF can be made immunogenic by insolubilization via an immune complex.

EXAMPLE 3

Generation of monoclonal anti-idiotypic antibodies to human IgM

Monoclonal anti-idiotypic antibodies to human IgM present on the cell surface of B-cell lymphomas may be useful as therapeutic agents in the treatment of some forms of B-cell lymphoma. In order to speed up the generation of these antibodies, and in order to use only small quantities of a sometimes limiting IgM immunogen, an intrasplenic immunization approach was tested. Soluble human IgM injected intrasplenically was not an effective immunogen for generating hybridomas. However, as shown in Table 2, when the human IgM was complexed to protein A-Sepharose ® via murine monoclonal antibody to human IgM, the IgM became immunogenic, resulting in about 1% of the clones being directed to the antigen combining site of the human IgM myeloma protein.

TABLE 2

ASSESSMENT OF INTRASPLENIC IMMUNIZATION FOR THE PRODUCTION OF ANTI-IDIOTYPIC HYBRIDOMAS

| | Time Period Between Immunization and Fusion | | | | | |
|---|---|---|---|---|---|---|
| | 3 Days | | | 7 Days | | |
| Immunogen | ID$^a$ | ID-PAS$^b$ | ID-MAb-PAS$^c$ | ID | ID-PAS | ID-MAb-PAS |
| No. of wells seeded | 1380 | 552 | 552 | 1380 | 920 | 920 |
| Hybrid efficiency (%) | 7.5 | 98 | 98 | 0 | 40 | 40 |
| Wells containing secreted murine immunoglobulin (%) | 0 | 159 (29) | 210 (38) | 0 | 16 (1.7) | 56 (6.0) |
| Wells containing secreted idiotypic hybridomas$^d$ (%) | 0 | 3 (0.5) | 5 (0.9) | 0 | 3 (0.3) | 11 (1.2) |
| Wells demonstrating | 0 | 0 | 5 (0.9) | 0 | 13 (1.4) | 6 (0.7) |

TABLE 2-continued

ASSESSMENT OF INTRASPLENIC IMMUNIZATION FOR THE PRODUCTION OF ANTI-IDIOTYPIC HYBRIDOMAS

| | Time Period Between Immunization and Fusion | | | | | |
|---|---|---|---|---|---|---|
| | 3 Days | | | 7 Days | | |
| Immunogen | ID[a] | ID-PAS[b] | ID-MAb-PAS[c] | ID | ID-PAS | ID-MAb-PAS |
| anti-IgM reactivity | | | | | | |

All fusions were performed with the mouse myeloma cell line 8.653 at a fusion ratio of 4:1 spleen:myeloma cells. Following fusion, cells were distributed into 96-well plates so that approximately 2 × 10[6] cells were seeded into every well.
[a]Human IgM (idiotype) immunoglobulin only.
[b]Human IgM (idiotype) immunoglobulin complexed to protein A-Sepharose ®.
[c]Human IgM (idiotype) immunoglobulin complexed to protein A-Sepharose ® via a mouse monoclonal anti-human IgM bridge.
[d]Anti-idiotype hybridoma-containing wells were assayed by solid phase ELISA for binding to a pool of five human IgM paraproteins or to the IgM used for immunization.

The specificity of these anti-IgM idiotypic monoclonal anti-bodies was then examined. The murine monoclonal antibodies were assayed for binding to a panel of human IgM paraproteins and individual IgM preparations. Table 3 demonstrates that these monoclonal antibodies bound only to autologous IgM, but not to other IgM preparations, thus showing likely anti-idiotypic specificity.

gen also limit the potential use of the 250 kd component as a vaccine. However, generation of monoclonal anti-idiotypic antibodies that recognize MAb 9.2.27 could provide a substitute vaccine. A number of immunization methodologies were assayed, both in rats and mice, to determine the optimal method for inducing murine monoclonal anti-idiotypic antibodies to a murine monoclonal antibody. These methods included a traditional

TABLE 3

SELECTIVITY OF MURINE MONOCLONAL ANTI-IDIOTYPIC ANTIBODIES AS DETERMINED BY ELISA*

| | Monoclonal Antibodies Generated by Immunization with Patient IgM | | | | | | | | | | | | |
|---|---|---|---|---|---|---|---|---|---|---|---|---|---|
| | Anti-Patient HM | | | | | Anti-Patient GD | | | Anti-Patient LH | | Anti-Patient KT | | |
| Screening Immunoglobulin | HM-1 3[b] | HM-2 μ | HM-3 2a | HM-4 2b | HM-5 1 | GD-1 1 | GD-2 1 | GD-3 μ | LH-1 1 | LH-2 1 | KT-1 2a | KT-2 1 | KT-3 1 |
| HM (IgM) | 1.00[c] | 0.88 | 1.00 | 1.10 | 1.30 | 0.00 | 0.01 | 0.00 | 0.00 | 0.00 | 0.00 | 0.00 | 0.00 |
| GD (IgM) | 0.00 | 0.06 | 0.00 | 0.00 | 0.00 | 1.12 | 1.00 | 1.10 | 0.00 | 0.00 | 0.00 | 0.00 | 0.02 |
| LH (IgM) | 0.02 | 0.00 | 0.00 | 0.00 | 0.00 | 0.01 | 0.01 | 0.00 | 1.32 | 1.18 | 0.00 | 0.00 | 0.00 |
| KT (IgM) | 0.00 | 0.00 | 0.00 | 0.00 | 0.00 | 0.00 | 0.00 | 0.01 | 0.00 | 0.00 | 0.35 | 0.98 | 1.07 |
| DM (IgM) | 0.00 | 0.00 | 0.00 | 0.00 | 0.00 | 0.00 | 0.00 | 0.00 | 0.00 | 0.01 | 0.00 | 0.00 | 0.00 |
| Meloy (IgM)[d] | 0.03 | 0.00 | 0.00 | 0.00 | 0.00 | 0.00 | 0.00 | 0.00 | 0.00 | 0.02 | 0.01 | 0.00 | 0.02 |
| Cappel (IgM)[d] | 0.00 | 0.00 | 0.01 | 0.05 | 0.00 | 0.01 | 0.03 | 0.00 | 0.00 | 0.00 | 0.01 | 0.01 | 0.02 |
| NHS[e] | 0.00 | 0.00 | 0.00 | 0.00 | 0.00 | 0.00 | 0.00 | 0.00 | 0.00 | 0.00 | 0.00 | 0.00 | 0.00 |

Anti-idiotypes generated by the indicated patients' IgM were assayed by solid phase ELISA for binding to a series of IgM paraproteins. Results are expressed as the OD$_{405}$.
[a]Anti-idiotype monoclonal antibody designation.
[b]Immunoglobulin isotype and subclass of the anti-idiotype monoclonal antibody.
[c]Positive ELISA results are underlined.
[d]Pools of human IgM myeloma proteins; Meloy-5 donors, Cappel-12 donors.
[e]Normal human serum.

EXAMPLE 4

Generation of rat monoclonal anti-idiotypic antibodies against monoclonal antibody which recognizes a tumor-associated antigen of human melanoma cells Antibody 9.2.27, which recognizes a human melanoma-associated antigen (a 250 kd glycoprotein/proteoglycan complex, also referred to as "proteoglycan antigen"), is useful in tar-geting human melanoma cells in patients (Schroff et al., JNCI 74: 299, 1985; Oldham et al., J. Clin. Oncol. 2:1235, 1984). The antigen recognized by 9.2.27 represents a difficult biochemical purification task, because it requires selective extraction techniques combined with CsCl gradient centrifugation and antibody affinity chromatography. The antigen has only been isolated in small quantities, which have been insufficient for immunization. Insufficient quantities of antigen also limit the potential use of the 250 kd component as a vaccine. However, generation of monoclonal anti-idiotypic antibodies that recognize MAb 9.2.27 could provide a substitute vaccine. A number of immunization methodologies were assayed, both in rats and mice, to determine the optimal method for inducing murine monoclonal anti-idiotypic antibodies to a murine monoclonal antibody. These methods included a traditional immunization schedule employing soluble MAb together with Freund's adjuvant. Immunogens were also created by conjugating the MAb to an albumin carrier, with immunization across species barriers (into rats and hamsters) to enhance immunogenicity. None of these methodologies were successful in generating anti-idiotypic antibodies.

A protocol according to the present invention, utilizing MAb 9.2.27 insolubilized on protein A-Sepharose ®, was successful in generating anti-idiotypic antibodies in rats. The results are shown in Table 4.

The rat monoclonal antibodies were shown to bind to the immunizing MAb 9.2.27, but not to the same subclass or other subclasses of mouse monoclonal antibodies. Thus, insolubilizing a murine MAb via an immune complex may aid in decreasing self-tolerance to mouse monoclonal antibodies in mice or rats.

TABLE 4

SPECIFICITY OF RAT ANTI-9.2.27 IDIOTYPIC ANTIBODIES*

| Test Antibody | Monoclonal Rat Anti-Murine Idiotypic Antibodies | | | | | |
|---|---|---|---|---|---|---|
| | 9131A | 3A11G5 | 3A11F5 | 9129 | 85-25-3A | 85-25-3B |
| Control | 0.000 | 0.003 | 0.003 | 0.004 | 0.002 | 0.007 |
| MOPC 21 (G1)[a] | 0.010 | 0.028 | 0.025 | 0.033 | 0.013 | 0.014 |
| D$_3$ (G1) | 0.097 | 0.173 | 0.151 | 0.209 | ND | 0.014 |

TABLE 4-continued
SPECIFICITY OF RAT ANTI-9.2.27 IDIOTYPIC ANTIBODIES*

| Test Antibody | Monoclonal Rat Anti-Murine Idiotypic Antibodies ||||||
|---|---|---|---|---|---|---|
| | 9131A | 3A11G5 | 3A11F5 | 9129 | 85-25-3A | 85-25-3B |
| 9-2-27 (G2a) | 1.052 | >2.0 | >2.0 | >2.0 | 0.167 | 1.477 |
| RPC5 (G2a) | 0.074 | 0.095 | 0.085 | 0.130 | 0.024 | 0.018 |
| $D_3$ (G2a) | 0.112 | 0.120 | 0.133 | 0.187 | 0.008 | 0.004 |
| T101 (G2a) | 0.077 | 0.117 | 0.110 | 0.160 | 0.015 | ND |
| ZME (G2a) | 0.096 | 0.115 | 0.103 | 0.230 | 0.016 | 0.017 |
| MOPC 141 (G2b) | 0.022 | 0.028 | 0.022 | 0.033 | 0.012 | 0.006 |
| MOPC 195 (G2b) | 0.000 | 0.004 | 0.006 | 0.008 | 0.008 | 0.005 |
| FLOPC 21 (G3) | 0.000 | 0.017 | 0.015 | 0.024 | 0.010 | 0.003 |
| Y5606 (G3) | 0.052 | 0.000 | 0.000 | 0.000 | 0.010 | 0.003 |
| MOPC 104E (M) | 0.000 | 0.000 | 0.003 | 0.006 | 0.002 | 0.018 |
| TEPC 183 (M) | 0.000 | 0.035 | 0.036 | 0.054 | 0.010 | 0.000 |
| TEPC 15 (1) | 0.000 | 0.053 | 0.049 | 0.066 | ND | ND |

*Murine monoclonal antibody 9.2.27, which recognizes a human melanoma-associated antigen, was used as an immunogen in rats. The resultant rat anti-murine idiotype monoclonal antibodies were assayed by solid phase ELISA for binding to murine monoclonal antibodies or myeloma proteins, as indicated. A mouse anti-rat peroxidase conjugate was used in the solid phase ELISA.
"Immunoglobulin isotype and subclass corresponding to each test monoclonal antibody or myeloma protein are indicated in parentheses.

EXAMPLE 5

Generation of multiple monoclonal antibodies directed against a variety of epitopes of a human melanoma-associated proteoglycan antigen Insolubilized immune complexes were employed in immunization strategies designed to generate a large number of monoclonal antibodies to a human melanoma-associated proteoglycan antigen.

Three types of immunogens were used for generating antibodies to the proteoglycan antigen. The first was whole cells. The cell lines used for this purpose included A375 M/M, SK MEL-28, SK MEL-31 grown in DMEM with ten percent fetal bovine serum (J.R. Scientific, Woodland, Calif.) and A375 M/M grown in serum-free media (Iscove's medium with 5 mg/liter insulin and transferrin and 5 μg/liter selenium). Immunizations were once a week for three weeks, with $1 \times 10^6$ cells subcutaneously. A second immunogen was prepared from extracts of melanoma cells (e.g., FMX or SK MEL-28 absorbed to lentil-lectin- or wheat germ agglutinin-Sepharose 4B ® (Morgan et al., *Hybridoma* 3:233, 1984)). A third type of immunogen utilized insolubilized immune complexes (e.g., protein A-Sepharose ®-bound complexes of 9.2.27 and melanoma NP-40 extracts (Giardina et al., *J. Immunol. Meth.*, 89:1-7, 1986)). The second and third type of immunogens were injected once a week for six consecutive weeks before fusion. A fourth immunization schedule combined a whole cell priming dose with immune complex immunization (e.g., complex of beads covalently attached to goat anti-mouse IgG, 9.2.27 and melanoma NP-40 extracts), in which mice were immunized with a three injections of whole cells followed by two injections with the insolubilized immune complex.

Hybridomas were produced by the fusion of immunized spleen cells with P3/X63-Ag8-653 myeloma cells at a 10:1 spleen:myeloma ratio. The hybridomas were first examined for binding to melanoma cells, B cells, and T cells using an indirect two-stage immunoperoxidase procedure (Woodhouse et al., *J. Natl. Canc. Inst.* 74:383, 1985). Hybridomas positive for binding to melanoma cells, but negative for binding to B and T cells, were subsequently screened by flow cytometry.

Figure 3B:
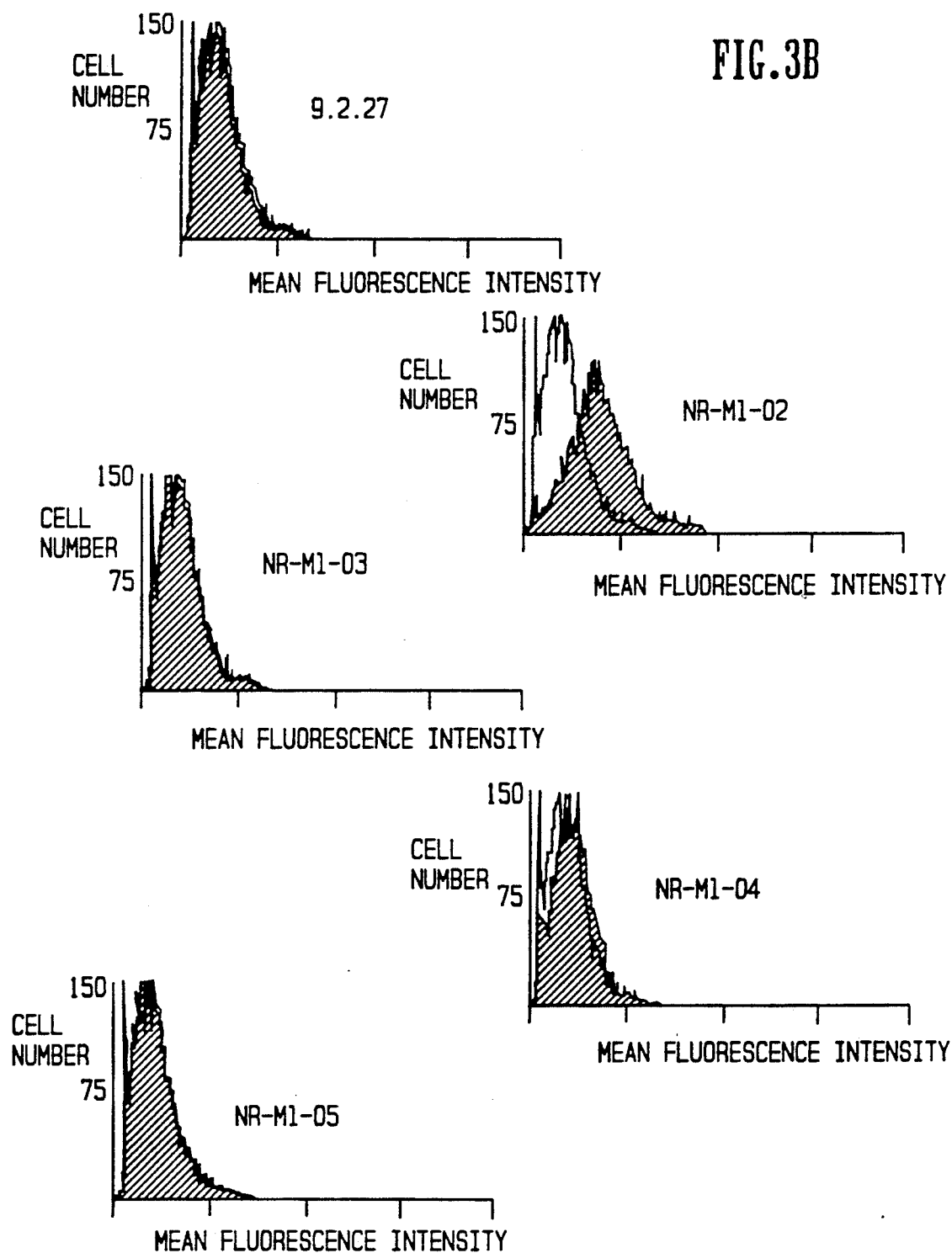
As shown in FIG. 3B, these same five anti-melanoma antibodies (9.2.27, NR-ML-02, NR-ML-03, NR-ML-04 and MR-ML-05) do not bind to A375 1° proteoglycan-negative cells.

Briefly, single cell suspensions of B and T cells and of A375 M/M proteoglycan-positive and A375 1° proteoglycan-negative melanoma cells were incubated with monoclonal antibodies at a concentration of 1 μg of antibody per $1 \times 10^6$ cells. Fluorescein isothiocyanate-conjugated goat anti-mouse antibody (Tago Inc., Burlingame, CA) was then used to detect bound monoclonal antibody. Target cell binding was analyzed on a Epics C cytofluorograph (Coulter Diagnostics, Hialeah, FL) using standardized fluorescein particles (Becton Dickinson, Mountain View, Calif.) to calculate free fluorescein equivalents. FIG. 3 shows the results obtained with MAb 9.2.27 and four melanoma-positive monoclonal antibodies that react with proteoglycan-positive cells (FIG. 3A), but do not bind to proteoglycan-negative cells (FIG. 3B).

Monoclonal antibodies reactive with the proteoglycan-positive melanoma cell line, but not with the normal or antigen-negative cell lines, were then examined in an indirect ELISA assay (Morgan and McIntyre, *Canc. Res.* 43:3155, 1983). The assay was performed with NP40 extracts of melanoma cells. A number of putative anti-proteoglycan monoclonal antibodies reacted with the melanoma cell extracts in a manner similar to MAb 9.2.27, while some did not react.

The monoclonal antibodies that produced ELISA patterns similar to MAb 9.2.27 were then further evaluated by an immunoperoxidase staining procedure using samples of human melanoma, skin and kidney. The latter two normal tissues represent all of the known normal tissue cross reactivities of 9.2.27. Monoclonal antibodies that intensely stained melanoma specimens, basal cells within epidermis of skin and collecting tubules in kidney were considered to be putative anti-proteoglycan antibodies ("9.2.27-like") and were investigated further.

A double determinant ELISA (two-site immunoassay) was performed to assess reactivity to proteoglycan. The double determinant ELISA was utilized in two formats. The first format utilized MAb 9.2.27 F(ab')$_2$ as capture antibody, with the addition of a standardized source of antigen, SK MEL-28 NP40 extract, followed by the addition of supernatants of putative anti-proteoglycan antibodies. Following incubation, bound monoclonal antibody was detected with a biotin anti-mouse Fc-specific reagent. Antibodies which gave positive color development in this assay were considered anti-proteoglycan antibodies. In a second format of the assay, the antigen in the extract was captured by solid-phase antibody, which included MAbs 9.2.27, NR-ML-02, NR-ML-03, NR-ML-04 and NR-ML-05. The same antibodies, biotinylated, were used in various combinations to detect bound antigen. Antibodies recognizing the same epitope under these conditions gave no color development, whereas antibodies recognizing distinctive epitopes gave significant color development. This assay assumes that only a single epitope per antibody is present on the antigen, which is tested by having both capture and detection with the same antibody.

Antibodies still showing reactivity at this level were evaluated by immunoprecipitation and SDS-PAGE to confirm the reactivity to the proteoglycan antigen. Five anti-proteoglycan antibodies were chosen for more detailed evaluation.

A summary of the number of fusions and the number of putative anti-proteoglycan antibodies is shown in Table 5.

TABLE 5

SUMMARY OF FUSIONS AND RESULTS

| Type of Immunogen | Number of Fusions | Number of Hybrids Screened | Number of Putative Anti-Proteoglycan MAbs |
|---|---|---|---|
| Lectin/Extract | 7 | 1,619 | 1 |
| Whole Cells | 7 | 1,767 | 4 |
| Immune Complex | 5 | 1,261 | 0 |
| Whole Cells plus Immune Complex | 2 | 1,302 | 67 |

Whole cell immunizations gave rise to relatively few putative anti-proteoglycan antibodies. However, the combination of sensitization with whole cells followed by boosting with the insolubilized immune complex of MAb 9.2.27 and proteoglycan antigen resulted in a large number of putative anti-proteoglycan antibodies. Five putative anti-proteoglycan monoclonal antibodies were selected for further analysis. These antibodies and the cell lines that produce them are shown in Table 6.

Deposits of the designated cell lines were made to the A.T.C.C., Rockville, Md., and were assigned the designated accession numbers.

TABLE 6

MONOCLONAL ANTIBODY AND HYBRID CELL LINE DESIGNATIONS

| Monoclonal Antibody | Hybrid Cell Line | ATCC Accession No. |
|---|---|---|
| NR-ML-02 | NR-ML-02 A1923 | HB-9352 |
| NR-ML-03 | NR-ML-03 A2215 | HB-9349 |
| NR-ML-04 | NR-ML-04 A1993 | HB-9351 |
| NR-ML-05 | NR-ML-05 A2106 | HB-9350 |
| NR-ML-06 | NR-ML-06 A3026 | HB-9348 |

The reactivity profiles of these antibodies are presented in Table 7.

TABLE 7

REACTIVITY OF ANTI-MELANOMA ANTIBODIES BY ELISA

| | Absorbance at 415 nm Against Target | | | | |
|---|---|---|---|---|---|
| ELISA TARGET | 9.2.27 | NR-ML-02 | NR-ML-03 | NR-ML-04 | NR-ML-05 |
| Pooled B&T cell cultures | 0.047 | 0.053 | 0.071 | 0.065 | 0.027 |
| Pooled melanoma cultures | 0.771 | 0.575 | 0.660 | 0.571 | 0.908 |
| A375 met mix melanoma cells | 1.097 | 0.886 | 0.961 | 0.688 | 1.036 |
| A375 primary melanoma cells | 0.007 | 0.001 | 0.018 | 0.018 | 0.051 |
| A375 met mix NP-40 extract | 1.008 | 0.772 | 0.808 | 0.774 | 1.130 |
| SK-MEL-31 NP-40 extract | 0.953 | 0.645 | 0.598 | 0.587 | 0.869 |

Detailed immunoperoxidase evaluation of the anti-proteoglycan monoclonal antibodies was performed. The patterns of reactivity were identical to MAb 9.2.27, including a low degree of antigenic heterogeneity as evidenced by intense and homogeneous staining of representative melanoma sections, with all the antibodies staining virtually all of the tumor cells. Smooth muscle and endothelial cell reactivity was also found with all of the antibodies.

Epitope comparisons of the anti-proteoglycan monoclonal antibodies were also performed, using both double determinant and addition assays, in ELISA and flow cytometry formats, respectively. Table 8 indicates that MAbs 9.2.27, NR-ML-03 and NR-ML-05 did not give a positive signal when used for both capture and detection, suggesting that each recognizes a unique epitope. In contrast, MAbs NR-ML-02 and NR-ML-04 did not give a positive signal in any combination, and thus appear to recognize the same epitope.

TABLE 8

EPITOPE COMPARISONS BY DOUBLE DETERMINANT SOLID-PHASE ELISA

| Biotinylated Detector Antibody | Absorbance with Indicated Capture Antibody | | | | |
|---|---|---|---|---|---|
| | 9.2.27 | NR-ML-02 | NR-ML-03 | NR-ML-04 | NR-ML-05 |
| 9.2.27 | 0.016 | 1.657 | 1.554 | 1.558 | 1.167 |
| NR-ML-02 | 1.731 | 0.107 | 1.229 | 0.094 | 0.927 |
| NR-ML-03 | 0.636 | 0.527 | 0.054 | 0.575 | 0.406 |
| NR-ML-04 | 1.847 | 0.030 | 1.445 | 0.119 | 1.078 |
| NR-ML-05 | 0.928 | 0.880 | 0.901 | 0.740 | 0.121 |

Antigen source-melanoma patient ascites fluid

This hypothesis was confirmed by additive cell surface binding with flow cytometry. Using the fluorescence intensity of each antibody, Table 9 shows that combinations of antibodies recognizing distinct epitopes gave 100% or more of the theoretical sum of the fluorescence intensity of the two antibodies alone minus that of the control antibody. NR-ML-04 and NR-ML-02 gave only one-half the expected value, indicating that these MAbs recognize the same epitope. Sixty-one other anti-proteoglycan monoclonal antibodies were screened for additivity to the four determinants recognized by 9.2.27, NR-ML-03, NR-ML-05 and NR-ML-02/NR-ML-04. None of the 61 antibodies examined recognized the same epitope as MAb 9.2.27, the antibody used in the immune complex immunization scheme. Ten of the sixty-one antibodies appeared to recognize the same determinant as NR-ML-02 and NR-ML-04, whereas only three antibodies recognized the same determinants as NR-ML-03 or NR-ML-05. Forty-eight of the antibodies did not recognize an epitope identified by the five characterized antibodies.

TABLE 9

EPITOPE COMPARISONS BY INDIRECT IMMUNOFLUORESCENCE

|  | 9.2.27 | KD 200 | P97 | ZME 08 | NR-ML-02 | NR-ML-04 | NR-ML-05 |
|---|---|---|---|---|---|---|---|
| 9.2.27 | 96 | | | | | | |
| KD200 | 96 | 118 | | | | | |
| P97 | 92 | 107 | 119 | | | | |
| ZME08 | 86 | 58 | 95 | 99 | | | |
| NR-Ml-02 | 90 | 100 | 105 | 91 | 97 | | |
| NR-Ml-04 | 88 | 104 | 109 | 92 | 59 | | |
| NR-Ml-05 | 95 | 94 | 100 | 97 | 85 | 72 | 104 |
| NR-Ml-06 | 100 | N/D | N/D | N/D | N/D | N/D | N/D |

(Percent of theoretical staining intensity on cultured melanoma cells; N/D = not done)

Representative anti-proteoglycan monoclonal antibodies were then evaluated for Fc-mediated binding using THP-1, a continuous monocytic cell line that expresses Fc receptors for murine and human IgG, as shown in Table 10. Since the THP-1 cell line does not express receptors for IgG-1, binding of the IgG-1 anti-proteoglycan monoclonal antibodies (NR-ML-02 and NR-ML-04) was at background levels. Interestingly, the IgG-2b NR-ML-05 antibody also did not bind, whereas both IgG-2a antibodies, NR-ML-03 and 9.2.27, bound extremely well.

TABLE 10

Fc RECEPTOR BINDING COMPARISON BY FLOW CYTOMETRY

| Antibody | Isotype | Fluorescein Equivalents | Test: Control Ratio |
|---|---|---|---|
| Secondary Alone | — | 37,000 | 1.0 |
| NR-ML-02 | IgG1 | 43,000 | 1.2 |
| NR-ML-04 | IgG1 | 61,000 | 1.6 |
| NR-ML-05 | IgG2b | 55,000 | 1.5 |
| NR-ML-03 | IgG2a | 186,000 | 5.0 |
| 9.2.27 | IgG2a | 196,000 | 5.3 |

The proteoglycan epitope recognized by MAb 9.2.27 exhibits trypsin-sensitivity (A. C. Morgan, Jr. et al., *Hybridoma* 1:27, 1981). Because trypsin-sensitivity may relate to relative exposure of an epitope at a target cell membrane, epitopes of the anti-proteoglycan antibodies generated herein were examined for trypsin-sensitivity.

Figure 4:
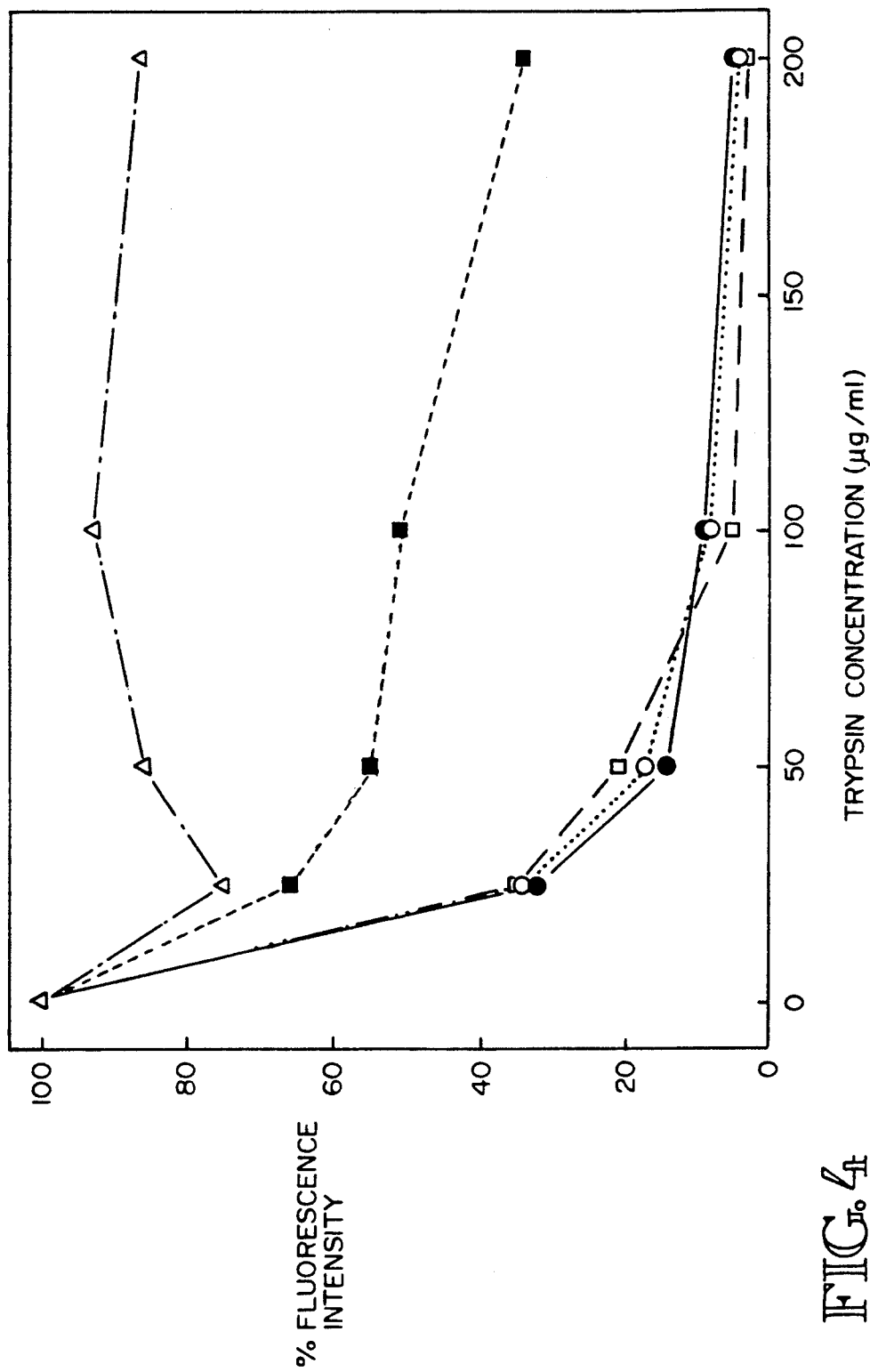
FIG. 4 depicts trypsin-sensitivity of epitopes recognized by anti-proteoglycan monoclonal antibodies. 9.2.27 (○); NR-ML-03 (□); NR-ML-04 (●); NR-ML-05 (■); and anti-HLA W6/32 (△).

FMX cells were exposed to varying concentrations of trypsin, and binding of monoclonal antibodies was evaluated by flow cytometry and expressed as percent fluorescence intensity of untreated FMX cells. FIG. 4 shows two classes of trypsin-sensitive epitopes. The first, epitomized by MAb 9.2.27, was highly trypsin-sensitive, requiring only low levels of trypsin to reduce antibody binding. This was in contrast to the relative trypsin-resistance of the HLA-A,B,C determinant recognized by MAb W6/32 and the epitope recognized by NR-ML-05. Trypsin-resistant epitopes may be located relatively close to the plasma membrane. Of 46 different anti-proteoglycan monoclonal antibodies examined, twenty recognized epitopes that were trypsin-sensitive.

Radiolabeled NR-ML-02, NR-ML-05 and 9.2.27 were further evaluated by biodistribution and tumor uptake in nude mice xenografts. Table 11 presents tumor localization of monovalent fragments of 9.2.27, NR-ML-02 and NR-ML-05.

TABLE 11

TUMOR LOCALIZATION OF ANTI-PROTEOGLYCAN ANTIBODIES ASSESSED BY BIODISTRIBUTION IN NUDE MICE CARRYING MELANOMA XENOGRAFTS

| Antibody | Type of Fragment | Number of Determinations | Average Tumor % Dose/Gram | Average Tumor: Blood |
|---|---|---|---|---|
| 9.2.27 | Fab | 16 | 2.08 ± 0.55 | 10.83 ± 2.87 |
| NR-ML-02 | Fab' | 8 | 2.05 ± 0.51 | 3.79 ± 1.31 |
| NR-ML-05 | Fab | 113 | 2.75 ± 0.74 | 23.96 ± 16.83 |

Papain digestion of 9.2.27 and NR-ML-05 produced Fab fragments; NR-ML-02 Fab' fragments were produced by pepsin digestion followed by cysteine reduction. Monovalent fragments were labeled with technetium-99m using a preformed diamido-dimercapto ligand system (European Patent Application 0188256) and injected intravenously at a dose of 50 mg per mouse. At 20 hours post-injection the mice were sacrificed, appropriate tissues were removed, weighed and counted, and data were corrected for isotopic decay.

Tumor uptake, as assessed by percent of injected dose per gram of tumor, was not significantly different for either NR-ML-02 or NR-ML-05 compared with 9.2.27 by a t-test (p>0.05). While 9.2.27 had a higher tumor:blood ratio than NR-ML-02 (p<0.01), the tumor:blood ratio for NR-ML-05 was higher than for either of the other two monoclonal antibodies (p<0.01).

The higher tumor uptake of NR-ML-05 cannot be attributed to antibody affinity, since the affinity of NR-ML-05 Fab is lower than the affinity of 9.2.27 Fab. In addition, 9.2.27 recognizes a greater number of binding sites on cultured cells than NR-ML-05. However, the tumor uptake of NR-ML-05 may correlate with proteolytic digestion within necrotic regions of the tumor, since NR-ML-05 is relatively trypsin-resistant.

EXAMPLE 6

Production of second generation monoclonal antibodies using NR-LU-10 - antigen immune complexes Insolubilized immune complexes were employed in immunization protocols designed to generate "NR-LU-10-like" monoclonal antibodies.

Briefly, two BALB/c mice were injected intraperitoneally with $10^7$ LS-174 colon carcinoma cells on days 1, 7, 14, 21 and 28. The mice were injected intravenously with insolubilized immune complexes on days 35, 44 and 51. Insolubilized immune complexes were formed by combining 200 μl of a 1% solution of goat anti-mouse IgG beads (Kirkegaard & Perry Laboratories, Inc., Gaithersburg, MD), 5 mg NR-LU-10 and LS-174 NP-40 extract (about 100 μg protein). The mice were sacrificed on day 54, and the spleens were harvested and frozen in liquid nitrogen.

In a first fusion performed with the frozen spleen cells, hybridomas were produced by the fusion of $7 \times 10^7$ immunized spleen cells and $1.5 \times 10^7$ P3/X63-Ag8-653 myeloma cells (5:1 spleen:myeloma). The resulting hybridomas were examined by ELISA techniques for binding to LS-174 NP-40 extract and to antigen captured by NR-LU-10. Hybridomas positive for binding to both LS-174 NP-40 extract and to NR-LU-10-captured antigen, or to NR-LU-10-captured antigen only, were further cloned and retested in the same ELISA. This fusion generated two hybridoma clones that secreted IgG3 antibodies that were positive in the two-site immunoassay. By immunohistology, these monoclonal antibodies displayed a tissue distribution similar to that of NR-LU-10. The hybridoma clones were designated A5792 and A5793 (secreting NR-LU-02 and NR-LU-03 monoclonal antibodies, respectively), and have been assigned ATCC Accession Nos. HB 10193 and HB 10194, respectively.

In a second fusion performed with the same frozen spleen cells, hybridomas were produced by the fusion of $1.7 \times 10^8$ immunized spleen cells and $2.3 \times 10^7$ P3/X63-Ag8-653 myeloma cells (7:1 spleen:myeloma). When tested as described for the first fusion, the second fusion generated one hybridoma clone producing a "NR-LU-10-like" IgG3 antibody, as determined by two-site immunoassay and immunohistology. This hybridoma clone was designated A5791 (secreting NR-LU-01 monoclonal antibody), and has been assigned ATCC Accession No. HB 10192.

Another immunization protocol included intraperitoneal injection of two BALB/c mice with 250 μl packed volume of an LS-174(NP-40) extract bound to Concanavalin A agarose on days 1, 7, 12 and 21. On days 28, 35 and 42, the mice were intravenously injected with insolubilized immune complexes formed by combining 200 μl of a 1% solution of goat anti-mouse IgG methacrylate beads, 5 mg NR-LU-10 and LS-174(NP-40) extract (about 100 μg protein). The mice were sacrificed on day 45, the spleens removed, and $10^8$ spleen cells were fused with $2 \times 10^7$ P3/X63-Ag8-653 myeloma cells. One hybridoma clone, designated NR-LU-05, was identified that was positive in the two-site immunoassay and showed a similar tissue distribution to NR-LU-10 by immunohistology.

Each of the above-described fusion protocols generated additional hybridoma clones that were positive in the two-site immunoassay, but which showed a tissue specificity different from that of NR-LU-10 by immunohistology. These monoclonal antibodies may recognize epitopes of the antigen which are shared with other, more widely represented tissue antigens.

EXAMPLE 7

Production of monoclonal antibodies directed against a cytotoxic trichothecene

Insolubilized immune complexes were employed in an immunization protocol designed to generate anti-verrucarin A monoclonal antibodies.

Verucarin A is a member of a group of small molecules (i.e., 400–600 daltons) called trichothecenes, which are a species of mycotoxins produced by soil fungi of the class *Fungi imperfecti* or isolated from *Baccharus megapotamica*. Trichothecenes are extremely potent cytotoxins that act at the ribosomal level to inhibit either initiation, elongation or termination of protein synthesis.

In order to generate antibodies to verrucarin A (VA), the toxicity of the molecule must be greatly reduced or eliminated. Further, due to the small size of VA (502 daltons), VA requires association with a carrier to be an effective immunogen. Conjugation of VA and targeting protein provides an avenue whereby the cytotoxicity of VA is decreased while its immunogenicity is increased.

Briefly, two BALB/c mice were injected intrasplenically on days 1 and 11 with 1 μg VA-monoclonal antibody conjugate that was insolubilized using 100 μl of a 1% solution of goat anti-mouse IgG methacrylate beads. The monoclonal antibody, NR-ML-05, was a murine IgG$_{2b}$ directed against a melanoma-associated proteoglycan. The mice were sacrificed on day 14 and the spleens were harvested.

Hybridomas were produced by the fusion of about $1 \times 10^8$ immunized spleen cells (obtained from combined spleens) and $2 \times 10^7$ P3/X63-Ag8-653 myeloma cells (5:1 spleen:myeloma). The hybridomas were screened by ELISA for binding to a human serum albumin (HSA)-VA conjugate and to HSA alone. Of 30 wells displaying growth, two hybridoma clones produced antibody reactive with HSA-VA, but not with HSA alone. To confirm that these hybrids recognized VA and not a "neo-determinant" expressed on the VA conjugate, hybridoma supernatants were tested for reactivity with two antibody-VA conjugates produced using different chemical linkages, and were found to be positive against both. Furthermore, free VA was shown to inhibit binding of both monoclonal antibodies to HSA-VA. These monoclonal antibodies, both of the IgM class, were designated NR-Va-01 and NR-Va-02.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

What is claimed is:

1. A method for producing a monoclonal antibody specific for an epitope distinct from that recognized by an existing monoclonal antibody, comprising the steps of:
    absorbing a first monoclonal antibody directed against a first epitope of a polyvalent antigen onto an inert, insoluble matrix capable of binding immunoglobulin, thereby forming an immunosorbent;
    combining said immunosorbent with said polyvalent antigen, forming an insolubilized immune complex wherein said first epitope is masked by said first monoclonal antibody;
    immunizing an animal with said insolubilized immune complex;
    fusing spleen cells from said immunized animal to myeloma cells to form a hybridoma capable of producing a second monoclonal antibody directed against a second epitope of said polyvalent antigen;
    culturing said hybridoma to produce said second monoclonal antibody; and
    collecting said second monoclonal antibody as a product of said hybridoma.

2. The method of claim 1 wherein said inert, insoluble matrix capable of binding immunoglobulin is selected from the group consisting of CNBr-activated agarose, CNBr-activated Sepharose ®, protein A-agarose, protein A-Sepharose ®, protein A-methacrylate beads, and anti-immunoglobulin-coated methacrylate beads.

3. The method of claim 1, comprising, after the step of absorbing the antibody, the additional step of cross-linking the antibody to the inert, insoluble matrix.

4. The method of claim 1, comprising, after the step of combining the antigen, the additional step of cross-linking the antibody and antigen.

5. The method of claim 1 wherein said antigen is a component of a heterogeneous mixture.

6. The method of claim 5 wherein said heterogeneous mixture is selected from the group consisting of human melanoma cell extract, human colon carcinoma extract, human breast carcinoma extract, and human lung carcinoma extract.

7. The method of claim 1 wherein said first epitope is a tumor-associated epitope recognized by monoclonal antibody NR-LU-10.

8. The method of claim 1 wherein the antigen is a tumor-associated antigen.

9. The method of claim 1 further comprising, after the step of culturing, the step of screening hybridoma culture medium to determine the presence of said second monoclonal antibody.

10. The method of claim 9 wherein the screening step is performed by double determinant ELISA.

11. The cell line NR-LU-01 A5791.

12. A monoclonal antibody produced by the cell line of claim 11.

13. The cell line NR-LU-02 A5792.

14. A monoclonal antibody produced by the cell line of claim 13.

15. The cell line NR-LU-03 A5793.

16. A monoclonal antibody produced by the cell line of claim 15.

* * * * *